United States Patent [19]

Dombek

[11] Patent Number: 4,590,216

[45] Date of Patent: May 20, 1986

[54] PROCESS FOR THE MANUFACTURE OF ALCOHOLS USING RUTHENIUM AND LANTHANIDE CATALYSTS

[75] Inventor: Bernard D. Dombek, Charleston, W. Va.

[73] Assignee: Union Carbide Corporation, Danbury, Conn.

[21] Appl. No.: 648,028

[22] Filed: Sep. 7, 1984

[51] Int. Cl.$^4$ .............................................. C07C 27/06
[52] U.S. Cl. ................................. 518/700; 502/224; 502/302; 502/303; 502/304
[58] Field of Search .......................................... 518/700

[56] References Cited

U.S. PATENT DOCUMENTS 4,301,253 11/1981 Warren ............................... 518/700
4,436,837 3/1984 Lin ..................................... 518/700

OTHER PUBLICATIONS

Warren et al., J of Catalysis 79, 334–347 (1983).

*Primary Examiner*—Howard T. Mars
*Attorney, Agent, or Firm*—Bernard F. Crowe

[57] ABSTRACT

A process for preparing low molecular weight alcohols from synthesis gas employing a homogeneous catalyst system of a ruthenium carbonyl complex and rare-earth containing complex.

30 Claims, No Drawings

PROCESS FOR THE MANUFACTURE OF ALCOHOLS USING RUTHENIUM AND LANTHANIDE CATALYSTS

This invention relates to an improved process and the catalyst system which achieves this process for making low molecular weight alkanols, especially methanol and ethanol directly from synthesis gas, i.e., mixtures of hydrogen and carbon monoxide.

BACKGROUND OF THE INVENTION

In U.S. Pat. No. 4,434,247 issued Feb. 28, 1984, there is disclosed a process for producing methanol, ethanol and ethylene glycol from synthesis gas employing a homogeneous ruthenium catalyst, preferably with a Lewis base promoter. It is always desired to improve such processes to achieve higher reaction rates and further selectivity of the final product.

Others have previously attempted to improve the activity or selectivity of homogeneous ruthenium catalysts for alcohol production by the addition of various promoters or co-catalysts. For example, in U.S. Pat. No. 4,332,914 issued June 1, 1982 it is said that halogen-free rhenium or manganese compounds added to a ruthenium catalyst dispersed in a low-melting quaternary phosphonium base or salt serve to increase the selectivity to methanol. In U.S. Pat. No. 4,332,914, issued June 1, 1982 it is said that the presence of a cobalt compound in a similar ruthenium catalyst system improves the selectivity to ethanol. It is further alleged in U.S. Pat. No. 4,339,545 issued June 13, 1983, that the addition of halogen-free titanium or zirconium compounds to a ruthenium catalyst in a low-melting quaternary phosphonium or ammonium base or salt increases the selectivity toward ethanol. In U.S. Pat. No. 4,436,837 issued Mar. 13, 1984 it is noted that a combination of a ruthenium compound, a samarium compound, a quaternary phosphonium salt, and an inert oxygenated solvent provides a catalytic system with improved selectivity to ethanol.

In none of these patents however is it said or shown that the total activity (total yield of methanol, ethanol and other organic products) can be increased by the added metal complex. Indeed, where direct comparisons are possible, as in U.S. Pat. No. 4,436,837, it is apparent that the total activity has been lowered by the added metal complex. The effect of the additional metal complex is apparently only to change the product distribution, not the rate of total product formation.

Lanthanides were said to be useful as co-catalysts with nickel and a halogen promoter in the carbonylation of an alcohol to its corresponding carboxylic acid in U.S. Pat. No. 4,426,537, issued Jan. 17, 1984. Other catalyst systems employing a lanthanide and aluminum are disclosed in U.S. Pat. No. 3,867,312 issued Feb. 18, 1975 and U.S. Pat. No. 4,429,089 issued Jan. 31, 1984. In none of such catalyst systems were lanthanides employed with ruthenium, nor were alkanols prepared from synthesis gas.

It is, accordingly, desired to increase the activity and/or selectivity of the homogeneous catalysts based upon ruthenium to convert synthesis gas to the desired alcohols at higher rates and with the capacity to selectively produce higher proportions methanol or ethanol and lower proportions of ethylene glycol.

SUMMARY OF THE INVENTION

The above and other objects are attained in an improved process for preparing low molecular weight alcohols by reacting hydrogen and carbon monoxide in the presence of a homogeneous catalyst system comprising a solubilized ruthenium carbonyl complex and a rare earth containing complex.

As employed herein the phrase "rare earth containing complex" includes (i) a compound containing a rare earth; that is, an element of the lanthanide series from atomic number 57 to 71 of the Periodic Table of Elements, (ii) yttrium and (iii) hafnium. The rare-earth containing complex is also referred to as the "co-catalyst".

In a more preferred embodiment the co-catalyst is selected from the group consisting of compounds containing Y, La, Ce, Pr, Nd, Sm, Er, Tm, Yb, Lu and Hf. Best results are obtained wherein the co-catalyst is selected from compounds containing La, Ce, Yb and Lu.

The invention is a process for selectively converting synthesis gas to a mixture of low molecular weight alcohols, such as $C_1$-$C_3$ alcohols, including mono- di- and tri-hydric alcohols. Products produced by the process include: glycerol, 1,2 propylene glycol, 1-propanol and methyl formate. However, the process is primarily concerned with producing $C_1$ and $C_2$ alkanols, especially methanol and ethanol, at higher rates and in selective proportions. The process can be oriented to enhance selectivity in favor of methanol or ethanol.

The process of this invention is carried out with the catalyst system dissolved in a solvent, even though such catalyst system may exist during the reaction in more than one liquid phase. In this sense, the reaction is termed a homogeneous liquid phase reaction.

There may be more than one such phase existing in the reaction zone, but the ruthenium and rare earth catalysts are always dissolved in at least one of such phases and are always in a dissolved liquid state. The problem with heterogeneous ruthenium-containing-catalysts in the reaction zone is that such will induce the Fischer-Tropsch reaction resulting in the formation of hydrocarbons and/or a variety of oxygenated hydrocarbons having a variety of molecular weights with low selectivity to any one compound. In fact the presence of such products suggests that undissolved ruthenium catalyst is present.

The process of this invention involves the solubilization of ruthenium and a rare earth co-catalyst in the presence of synthesis gas at such temperatures and pressures, and for a period of time sufficient to produce the desired alcohols. Such conditions are set forth herein.

The process of this invention is distinctive in the selection of materials which comprise the homogeneous liquid phase mixture, the reaction parameters and the stability of the ruthenium and rare earth containing complexes. As with any technology, this process has undergone evolutionary changes and its further examination will undoubtedly bring about more changes, most likely in the form of additional or substitutional steps and/or materials.

In the preferred form of the invention the process is carried out in the presence of a promoter. A promoter, in the context of this invention, is a material provided to the reaction which causes a promotional effect in that it enhances the production (viz., rate, yield or efficiency) of any of the products, or it improves the selectivity of the reaction toward methanol or ethanol or it helps to reduce the loss of catalyst during the reaction. A promoter may be any Lewis base containing compound. Any Lewis base may be a promoter, but all Lewis bases will not serve to act as a promoter under any given set of reaction conditions. The effectiveness of the Lewis base as a promoter will in large measure be dependent upon the reaction conditions selected. Operation of the process in the absence of the Lewis base promoter will result in most instances in less productivity and, accordingly, exploitation of the process in a commercial sense will probably necessitate the use of a promoter.

The amount of Lewis base promoter added to the process is that amount which provides the promotional effect. The maximum amount employed is that amount whose presence is too costly for the economical operation of the process, or substantially reduces the promotional effect without any advantages, or provides no advantages in the operation of the process, or a combination of these factors. The promoter can be a material used in miniscule quantities to a material employed in maximum quantities, such as a solvent for the reaction and the ruthenium-rare earth catalysts. Indeed, the promoter can be a material such as carboxylic acids, which, when present, react with the products of the reaction.

The selections of solvent and promoter are not narrowly limited, yet there appears to be some degree of cooperation that each imparts to the success of the process and the selection of one often-times dictates the selection of the other in order to maximize the benefits of the invention.

It is found necessary that there be used a solvent that is capable of maintaining the chosen catalyst system, optionally the Lewis base promoter (if it is not the solvent), in the homogeneous liquid phase mixture throughout the reaction. This appears to be the prime function of the solvent. The solvent may possibly provide an additional benefit, such as influencing the kinds of ion pairing that exist during the course of the reaction.

DETAILED DESCRIPTION OF THE INVENTION

The catalyst system of this invention contains a ruthenium complex and a rare-earth metal complex. The ruthenium complex contains carbon monoxide directly bonded to ruthenium (ruthenium carbonyl). The ruthenium compound which is provided to the reaction is not necessarily in a form which will effectively catalyze the reaction even if it contains a carbon monoxide ligand bonded to it. Ruthenium compounds such as ruthenium salts, oxides and carbonyl clusters may be introduced to the reaction in a condition which allows them to be solubilized, and under the conditions of the reaction they are converted into a carbonyl complex which effectively catalyzes the reaction. That is why they are defined in terms of products made by the process.

The composition and structure of the ruthenium carbonyl complex which catalyzes the desired reaction is not specifically known. It may be a monoruthenium or polyruthenium compound. Illustrative of polyruthenium compounds are the well-known cluster compounds of ruthenium. However, the addition of a cluster, containing only a carbonyl ligand such as $Ru_3(CO)_{12}$ does not alone create the catalyst and, as such, cause the catalytic reaction. Some modification of such structure is needed, possibly the destruction of the cluster structure to a mononuclear ruthenium structure. Factors to be considered in achieving the catalyst are the reaction parameters, the choice of solvent and, optionally, the Lewis base promoter, if employed. Because varied reaction conditions and solvents, with and without promoters, result in different amounts of the desired products of the process, and different rates, efficiencies and/or yields, it is presumed that each provides a different and distinct catalytic environment.

The ruthenium-containing substances which may be employed in the practice of this invention to form the catalyst under process conditions encompass those which are described, for example, in Gresham, U.S. Pat. No. 2,535,060 at column 2, starting at line 38 to line 48, and ruthenium carbonyl compounds. It is not advisable to place ruthenium compounds or substances on a support material for use in the process of this invention because it offers no benefits over solubilizing such ruthenium compounds in combination with the aforementioned solvent and Lewis base promoter. Moreover, ruthenium deposited on a support material can be expected to be solubilized in the homogeneous liquid phase reaction system of this invention as it is contacted with carbon monoxide. Even ruthenium metal in the presence of the solvent, carbon monoxide and hydrogen can be converted to a ruthenium carbonyl complex which is soluble. Ruthenium oxides, such as dioxide, sesquioxide, or tetraoxide, are capable under appropriate conditions of being solubilized and converted to a carbonyl complex which can be used to form the catalyst under the conditions of this process. However, when using such insoluble ruthenium compounds, they must first be solubilized before the effective operation of the process of this invention.

Ruthenium carbonyl compounds (which include ruthenium carbonyl hydrides or ruthenium carbonyl clusters) are already provided with a carbonyl ligand, and under the conditions of the reaction can be sufficiently changed to achieve the desired catalytic effect. Ruthenium salts such as those of organic acids can be employed in the practice of this invention to produce the catalyst. In addition to those ruthenium compounds described in the aforementioned Gresham patent, one may employ ruthenium compounds of bidentate ligands, allyl complexes, arene complexes, halides, and alkyl complexes. The choice of ruthenium compounds is varied and not critical to this invention. A number of ruthenium complexes are known to be more stable to the presence of carbon monoxide than other ruthenium compounds and the skilled worker can determine which particular ruthenium compound might take longer to initiate a reaction than other ruthenium compounds. On that basis, one can select for the purposes of convenience the particular ruthenium compound to be utilized in forming the catalyst. Howover, ruthenium which is associated with an organic molecule or complexed with carbon monoxide is most readily solubilized so as to provide the ruthenium catalyst of this process.

The rare-earth containing substances employed as the co-catalyst are varied. The rare-earth complex must be solubilized in-situ or prior to reaction in order to co-act with the ruthenium complex to catalyze the conversion of synthesis gas to the desired end products, especially methanol and ethanol. The rare-earth element can be employed as an inorganic or organic complex, as a mixture of either or both. For example, it may be utilized in a salt form as a halide, hydroxide, oxychloride, carbonate, oxalate, carboxylate ($R_1COO—$) or the like.

In addition, the rare-earth element can be employed as a complex in which a ligand is bound to the element.

That ligand can be any suitable organic ligand, as described above, including a monovalent or monodentate organic radical, such as an amide ($-NR_1C(O)R_2$); an alcoholate ($OR_1$); a dialkylamide ($-NR_1R_2$); and others, wherein $R_1$ and $R_2$ are the same or different and are alkyl cycloalkyl or aryl having 1 to 20 carbon atoms.

The rare-earth elements include: a metal of the lanthanide series with an atomic number from 57 to 71 of the Periodic Table; yttrium and hafnium. It has been found that lanthanides with an atomic number in the middle of the lanthanide series are less effective for promoting the reaction. The factors responsible for this effect are not yet completely understood. Accordingly, while only certain preferred lanthanide elements have been shown to increase the rate of methanol production at least to a degree of several times that of a system not containing such nevertheless it is believed that with proper selection of reaction ingredients and parameters, all such rare-earth elements of the invention will eventually provide satisfactory results. All the catalysts of ruthenum and rare-earth elements of the invention tested, reduced the rate of ethylene glycol formation, as compared to a ruthenium based catalyst system.

Based on the results observed, enhanced results for methanol and/or ethanol promotion are obtained from a co-catalyst selected from a bimodal distribution of the lanthanide series. Accordingly, a preferred class of co-catalysts of the invention includes those containing Y, La, Ce, Pr, Nd, Sm, Er, Tm, Yb, Lu and Hf.

Best results are obtained when the co-catalyst is one selected either at the beginning or at an end of the lanthanide series, and, especially lanthanum, cerium, ytterbium and lutetium.

The salts of the rare earth elements, such as the oxides, and, especially, the halides, particularly the chlorides, are most effective. Examples of such salts include: $La_2O_3$, $Yb_2O_3$, $Ce(CH_3C(O)CHC(O)CH_3)_3$, $YCl_3$, $LaCl_3$, $CeCl_3$, $PrCl_3$, $SmCl_3$, $ErCl_3$, $TmCl_3$, $YbCl_3$, $LuCl_3$, and $HfCl_3$, and mixtures thereof.

As characterized above, this process is operated as a homogeneous liquid phase mixture. The process is typically carried out in a solvent for the catalyst system and the Lewis base promoter, when added. Thus the solvent is a liquid in which the catalyst system and the added Lewis base promoter are soluble under the prescribed conditions of the reaction. The solvent may be solid at room temperature but should, at least in part, be a liquid under the conditions of reaction.

A preferred solvent is a liquid at reaction conditions which is polar or complexes ions. Of the polar solvents those which have a relatively high dielectric constant are more preferred. As for the solvents which complex ions, the desirable solvents are those which, under the reaction conditions, have the capacity of complexing ions such as available cations. As stated previously, the solvent may provide the Lewis base component. Solvents having a dielectric constant at 25° C., or at its melting temperature, whichever is higher, of greater than 2 are preferred.

Illustrative of suitable polar solvents are, e.g., water, ketones, esters including lactones, amides including lactams, sulfones, sulfoxides, halogenated hydrocarbons, aromatic hydrocarbons, and the like. Illustrative of specific solvents encompassed by the above classes of polar solvents are, for example, aromatic hydrocarbons, e.g., benzene, toluene, xylene, naphthalene, alkylnaphthalene, etc.; carboxylic acids such as acetic acid, propionic acid, butyric acid, caproic acid, stearic acid, benzoic acid, cyclohexane-carboxylic acid, ketones such as acetone, methyl ethyketone, cyclohexanone, cyclopentanone, etc.; esters such as methyl acetate, ethyl acetate, propyl acetate, butyl acetate, methyl propionate, ethyl butyrate, methyl laurate, etc.; anhydrides such as phthalic anhydride, acetic anhydride, etc.; lactams such as N-alkyl caprolactam, such as N-methylcaprolactam, N-alkyl pyrrolidinones such as N-methyl pyrrolidinone; cyclic ureas such as N,N'-dimethylimidazolidone, polyols such as ethylene glycol, glycerine, erythritol, polyalkylene glycol containg two to about ten thousand repeating units; lactones such as gamma-butyrolactone; halogenated hydrocarbons such as chlorobenzene, chloroform, methylene chloride, 2,2-dichloropropane; amides such as dimethylformamide, dimethylacetamide, hexamethylphosphoramide; sulfones such as sulfolane, dimethylsulfone, substituted sulfolanes; sulfoxides such as dimethylsulfoxide, diphenyl sulfoxide; as well as many others.

Illustrative of suitable complexing solvents are the ethers, cryptands, and the like. Illustrative of specific solvents encompassed by the above classes of complexing solvents are, for example, ethers such as tetrahydrofuran, tetrahydropyran, diethyl ether, 1,2-dimethoxybenzene, 1,2-diethoxybenzene, the mono and dialkyl ethers of alkylene and polyalkylene glycols, such as ethylene glycol, of 1,2-propylene glycol, of 1,2-butylene glycol, of diethylene glycol, of di-1,2-propylene glycol, of triethylene glycol, of pentaethylene glycol (such as triglyme, tetraglyme and pentaglyme), of di-1,2-butylene glycol, of oxyethylene-oxypropylene glycols, etc., preferably those in which the alkylene group contains 2 and/or 3 carbon atoms in the divalent moiety, such as ethylene and 1,2-propylene; the cryptands such as described in U.S. Pat. No. 4,111,975, which description of cryptands, as promoters in that case, are incorporated herein by reference; the crown ethers (or Crown Ethers, as one may prefer) such as described in U.S. Pat. No. 4,162,261, which description of crown ethers, as solvents in that case, are incorporated herein by references; as well as many others.

The choice of solvent in any particular case can be a complex decision. Some solvents such as the carboxylic acids play a dual role in the practice of the process of this invention. They can provide the required Lewis base promoter as well as the solvent. Others solvents which can play this dual function include, e.g., the crown ethers and the cryptands, as well as many others. In many instances, solvents react with the products of the reaction and such reactive solvents are considered useful in the practice of this invention because the derivative products obtained are an excellent source for the desired products of the reaction. For example, the carboxylic acids are not only effective solvents and promoters, they are also reactive with ethylene glycol, methanol and ethanol products, to produce ethylene glycol dicarboxylates, methyl carboxylates, and ethyl carboxylates. These carboxylates can be readily hydrolyzed to produce the alcohol products. This is not necessarily an uneconomical method to produce such products. In many cases (and possibly in the preferred cases) another Lewis base promoter will be employed in combination with a solvent which has the capacity to serve in such dual function. This is because such other Lewis base promoter is found to be more effective in generating the desired products when used in combination with that solvent under the conditions of reaction chosen.

An important class of solvents contemplated in the practice of this invention are mixtures of the aforementioned polar solvents and the complexing solvents. Various polar solvents mixed with other polar or complexing solvents are contemplated to provide enhanced results either in terms of rates, selectivity, conversions and/or yields of one or more of the desired products. Which mixtures will achieve what result has not been determined. Combinations of, e.g., sulfolane with crown ethers, lactones, amides or ureas are contemplated as potentially useful. Combinations of, e.g., crown ethers with lactones, amides, and ureas are contemplated as potentially useful.

The Lewis bases suitable as promoters in the practice of this process are not a narrowly defined class of materials. They encompass a broad range of inorganic and organic materials, and all members of the class are contemplated as employable in the practice of this invention. Its effectiveness in some instances can be noted when used in as little an amount which is the least amount for which a measurable promotional effect is seen, to an amount wherein the Lewis base is also a solvent for the reaction. The Lewis base can serve a dual function by playing the role as the solvent for the reaction. There is no simple way of determining what Lewis base will function effectively under a given set of reaction conditions. In the typical case, when a Lewis base exhibits promotional effects on the rate of the reaction, it is present and dissolved in the liquid phase in a range of from about 0.01 mole to about $10^6$ moles for each atom (gram atomic weight) of ruthenium present in the reaction. More preferred, the Lewis base is present (even when the solvent used is a Lewis base) in the liquid phase in a range from 1 mole to about $10^4$ moles for each atom of ruthenium present in the reaction; most preferably, greater than one mole up to about 1000 moles of the Lewis base for each atom of ruthenium present and dissolved in the liquid phase.

The Lewis base promoters include inorganic as well as organic compounds. Illustrative of suitable organic compounds are those containing at least one Lewis base nitrogen atom or at least one Lewis base oxygen atom or a combination of such nitrogen and oxygen atoms. The carbon atoms can be part of an acyclic and/or cyclic radical such as aliphatic, cycloaliphatic and aromatic carbon radicals. Usually, the organic Lewis bases contain at least 2 carbon atoms and no more than 40 carbon atoms. The Lewis base nitrogen atoms are usually in the form of imino (—N═),

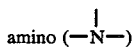
amino (—N—)

and nitrilo (N≡), etc. The Lewis base oxygen atoms can be in the form of groups such as hydroxyl (aliphatic or phenolic), carboxyl, carbonyloxy, oxy, carbonyl, etc. The organic Lewis bases may also contain other atoms and/or groups as substituents of the aforementioned radicals such as alkyl, aryl and chloro substituents. The Lewis base promoter also includes a variety of inorganic compounds such as, for example, inorganic amines and a variety of inorganic metal compounds.

Illustrative of suitable classes of Lewis base promoters are, for example, any of the following: monoamines and polyamines including those compounds in which Lewis base nitrogen forms part of a ring structure; alkanolamines; acyl compounds including aliphatic, cycloaliphatic and aromatic carboxylic acids, ester derivatives and anhydrides of such acids, usually having no more than 20 carbon atoms; bis(triorgano phosphine); iminimum compounds; ketones; ethers; amides; crown ethers; cryptands; hydroxides and salts of various metals including, for example, carboxylates, halides, carbonates, bicarbonates, sulfates and bisulfates of any of the alkali metals, alkaline earth metals as well as of other metals such as iron; as well as many other compounds which can function as Lewis bases or serve as a source for the Lewis base under reaction conditions.

Illustrative of specific Lewis bases are the following:
Methyl-, ethyl-, isopropyl- and octylamines
Dimethyl-, diisoamyl- and diisobutylamines
Methylethylamine
Trimethyl- and triethylamines
Methyldiethylamine
Triisobutyl- and tridecylamines
1,2-Ethanediamine
1,3-Propanediamine
Diethylenetriamine
Triethylenetetraamine
Tetraethylenepentaamine
 $NH_2CH_2CH_2NHCH_2CH_2NHCH_2CH_2NHCH_2CH_2NH_2$
N,N,N',N'-Tetramethylethylenediamine,
 $(CH_3)_2NCH_2CH_2N(CH_3)_2$
N-pentamethyldiethylenetriamine
p-Phenylenediamine
o-Toluidene
Aniline
1-Naphthyl- and 2-naphthylamines
p-Toluidine
Benzylamine
Diphenylamine
Dimethylaniline
Bis-(1,8)-dimethylaminonaphthalene
Cyclohexylamine
Dicyclohexylamine
Piperidine and N-methylpiperidine
3-Phenylpiperidine
Pyridine and 2-methylpyridine
2,4,6-Trimethylpyridine
2-Dodecylpyridine 2-Aminopyridine
2-(Dimethylamino)pyridine
Quinoline
2-(Dimethylamino)-6-methoxyquinoline
Pyrimidine
1,8-Phenanthroline
Piperazine
N-methyl- and N-ethylpiperazines
2,2'-Bipyridyl and alkyl-substituted 2,2'-bipyridyls
1,4-Diazabicyclo[2.2.2]octane ("triethylenediamine")
Hexamethylenetetraamine
Purine
Isopropanolamine
Diethanolamine
Di-n-propanalamine
Triethanolamine
Triisopropanolamine
Bis(dimethylaminoethyl)ether
N,N-dimethylglycine
N-methyliminodiacetic acid
2-Hydroxypyridine
2-Methoxypyridine
2,6-Dimethoxypyridine
4-Methyl-2-hydroxypyridine
4-Methyl-2,6-dihydroxypyridine Morpholine
N-methyl- and N-ethylmorpholines
Hexadecylmorpholine
Ethylenedimorpholine
Tetraethylenedimorpholine
Picolinic acid
Nitrilotriacetic acid
2,5-Dicarboxypiperazine
N-(2-hydroxyethyl)-iminodiacetic acid
2,6-Dicarboxypyridine
Ammonia
Hydroxylamine
Hydrazine
Hexamethylphosphoramide
Dimethylformamide
N-Methylpyrrolidinone
Acetic acid
Propionic acid
Butyric acid
2,2,6,6,-Tetramethylheptane-3,5-dione, $(CH_3)_3CC(O)CH_2C(O)C(CH_3)_3$
Sulfolane
18-Crown-6
15-Crown-5
Tetrahydrofuran
Diphenylether
Bis(triphenylphosphine)iminium chloride, $[C_6H_5)_3P]_2N+Cl-$
Bis(triphenylphosphine)iminium iodide, $[C_6H_5)_3P]_2N+I-$
Cesium formate
Sodium acetate
Sodium sulfate
Potassium carbonate
Potassium bicarbonate
Cesium oxide
Cesium hydroxide
Potassium hydroxide
Magnesium bromide
Calcium iodide
Cesium bromide
Sodium fluoride
Potassium fluoride
Rubidium bromide
Cesium iodide
Rubidium iodide
Potassium iodide
Sodium iodide
Sodium bromide
Lithium iodide
Lithium bromide
Lithium chloride
Potassium chloride
Lithium diethylamide
Sodium phenyl
Butyllithium
Cobalt diiodide, e.g. $CoI_2.2H_2O$
Tetracarbonyl cobaltate anion, $[Co(CO)_4]$-1
Ferrous iodide, e.g. $FeI_2.4H_2O$ Not all of the above Lewis bases, or for that matter all Lewis bases, will ncessarily function effectively in all of the embodiments of the process of this invention. In most cases a degree of selection between the choice of Lewis base, the amount of catalyst, the choice of solvent and the reaction parameters will be required to obtain the level of productivity sought.

Because $H_2$ is supplied to the reaction, a hydride of the lanthanide metal or ruthenium can exist in the reaction system. There is no appreciation of the particular role that hydride plays in the reaction. It is believed that either too much or too little hydrogen present in the reaction will not favor the production of the desired alcohols. In such a case, one can contemplate a role for hydride in the reaction mechanisms occurring.

In general, the halide-promoted and, especially, the iodide-promoted catalyst systems provide enhanced results. Lithium iodide, sodium iodide, potassium iodide, hydroiodic acid and iodine are the preferred promoters.

Where rare earth type halides, such as the lanthanide series trichlorides are employed as co-catalyst, it has been found that they can generate hydrochloric acid (HCl) upon hydrogen reduction or upon reaction with alcohol products. The activity of the instant catalyst system is reduced in the presence of HCl or other strong acids, since ruthenium compounds, especially in the presence of iodide ion, are subject to oxidation. Accordingly, it is desirable to reduce the amount of HCl formed in the process by adding a base to the system in sufficient amounts to neutralize any HCl produced. Typical bases include: $KHCO_3$; $NaHCO_3$; $Na_2CO_3$, $NaH_2PO_4$; $NaH_2SO_3$; $Na_2HSO_4$; $K_2CO_3$ and the like. The preferred base is $K_2CO_3$.

In general, the base is employed in amounts sufficient to neutralize the HCl produced by reduction of a lanthanide series metal chloride. For this and other purposes usually from about 1 to 5 equivalents base and, preferably, about one equivalent base per equivalent chloride in the lanthanide chloride is employed.

The catalyst system of the invention is capable of providing methanol and ethanol in greater amounts, than when only a ruthenium catalyst is employed. In addition, for most catalyst systems of the invention, the selectivity for methanol is improved.

If desired, selectivity toward ethanol can also be enhanced by careful control of the acidity (or oxidation state) of the reaction system. It has been found that the catalyst complexes of the invention in the presence of an iodide promoter, an acid and a phosphine oxide solvent, promote formation of ethanol.

It is possible that the acid facilitates formation of a methyl ligand or a methylidene complex, which is readily converteo to ethanol. The phosphine oxide solvent is believed to level the acidity of such added acid, while still permitting the presence of basic metal complexes also required in the system.

It has been found that addition of hydriodic acid or iodine to the catalyst system of the invention can act to serve as a source of both acid and iodine promoter. The iodine is converted to hydriodic acid or its equivalent under the catalytic conditions. The preferred phosphine oxide solvent is tri-n-propylphosphine oxide.

The relative amounts of carbon monoxide and hydrogen which are initially present in the reaction mixture can be varied over a wide range. In general, the molar ratio of $CO:H_2$ is in the range of from about 40:1 to about 1:40, suitably from about 20:1 to about 1:20 and preferably from about 10:1 to about 1:10. It is to be understood, however, that molar ratios outside the broadest of these ranges may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, the product alcohols are contemplated as obtainable by using mixtures containing carbon dioxide and hydrogen. Mixtures of carbon dioxide, carbon monoxide and hydrogen can also be employed. If desired, the reaction mixture can comprise steam and carbon monoxide.

The quantity of catalysts employed is not narrowly critical and can vary over a wide range. In general, the process is desirably conducted in the presence of a catalytically effective quantity of the active ruthenium species which gives a suitable and reasonable reaction rate.

Reaction can proceed when employing as little as about $1 \times 10^{-6}$ weight percent, and even lesser amounts, of ruthenium based on the total weight of reaction mixture (i.e., the liquid phase mixture). The upper concentration limit can be quite high, e.g., about 30 weight percent ruthenium, and higher, and the realistic upper limit in practicing the invention appears to be dictated and controlled by economics in view of the cost of ruthenium. Since the rate of conversion of synthesis gas may be dependent upon the concentration of ruthenium employed, (higher concentrations achieving higher rates), then large concentrations may prove to be a most desirable embodiment of this invention. Depending on various factors such as the Lewis base promoter (if employed), the partial pressures of carbon monoxide and hydrogen, the total operative pressure of the system, the operative temperature, the choice of solvent, and other considerations, a catalyst concentration of from about $1 \times 10^{-3}$ to about 10 weight percent ruthenium (contained in the complex catalyst) based on the total weight of reaction mixture is generally desirable in the practice of the invention.

The process is conducted in catalytically effective amounts of active rare-earth co-catalyst, sufficient to provide a suitable and reasonable reaction rate. In general, from about 0.01 to 100 times, by weight, of rare earth co-catalyst is employed, based on the weight of ruthenium present, although greater and lesser amounts can be employed. Enhanced results are obtained, and, accordingly, it is preferred to employ from about 0.1 to 10 times the amount of ruthenium present, especially when ruthenium is present in amounts from $10^{-3}$ to 10 weight percent based on the total reaction mixture. Most preferably, the molar ratio of rare earth to ruthenium is from about 2:1 to 1:2.

The temperature which may be employed in practicing the process may vary over a wide range of elevated temperatures. In general, the process can be conducted at a temperature between about 100° and about 400° C. and higher. Temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, catalysts, solvent, or Lewis base promoter instability may occur. Notwithstanding these factors, reaction will continue and the alcohols and/or their derivatives will be produced. Preferred temperatures are between about 150° C. and about 350° C.

The process is suitably effected over a wide superatmospheric pressure range. At pressures on the order of and below about 500 psia (35.15 kg/cm$^2$) the rate of desired product formation is quite slow, and consequently, relatively faster reaction rates and/or higher conversions to the desired products can be obtained by employing higher pressures, e.g., pressures of at least about 1,000 psia (70.31 kg/cm$^2$). Pressures as high as 20,000 to 50,000 psia (3,515.35 kg/cm$^2$), and higher, can be employed but there is no apparent advantage in using such pressures, and any advantage that could be reasonably contemplated would be easily offset by the very unattractive plant investment outlay required for such high pressure equipment and the costs associated with such high pressure operations. Therefore, the upper pressure limitation is approximately 15,000 psia (1,054.6 kg/cm$^2$). Effecting the process below about 10,000 psia (703.1 kg/cm$^2$), results in significant cost advantages which are associated with lower pressure equipment requirements and operating costs. A suitable pressure range is from about 1000 psia (70.31 kg/cm$^2$) to about 12,500 psia (878.84 kg/cm$^2$). The pressures referred to above represent the total pressure of hydrogen and carbon monoxide.

The process is effected for a period of time sufficient to produce the desired alcohol products and/or derivatives thereof. In general, the residence time to produce the desired products can vary from minutes to a number of hours, e.g., from a few minutes to 24 hours, and longer. It is readily appreciated that the residence period (time) will be influenced to a significant extent by the reaction temperature, the concentration and choice of Lewis base promoter, rare earth source, ruthenium source, the total gas pressure and the partial pressure exerted by its components, the concentration and choice of solvent, and other factors. The synthesis of the desired product(s) by the reaction of hydrogen with carbon monoxide is suitably conducted under operative conditions which give reasonable reaction rates and/or conversions.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperature due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art.

The catalyst precursor may be initially introduced into the reaction zone batchwise, or it may be continuously or intermittently introduced into such zones during the course of the synthesis reaction. Means to introduce and/or adjust the reactants, either intermittently or continuously, into the reaction zone during the course of the reaction can be conveniently utilized in the process especially to maintain the desired molar ratios of, and the partial pressures exerted by, the reactants.

As intimated previously, the operative conditions can be adjusted to optimize the conversion of the desired product and/or the economics of the process. In a continuous process, for instance, when it is preferred to operate at relatively low conversions, it is generally desirable to recirculate unreacted synthesis gas with or without make-up carbon monoxide and hydrogen to the reactor. Recovery of the desired product can be achieved by methods well-known in the art such as by distillation, fractionation, extraction, and the like. A fraction comprising catalyst complex, generally contained in byproducts and/or the solvent, can be recycled to the reaction zone, if desired. All or a portion of such fraction can be removed for recovery of the ruthenium or rare-earth metal values or regeneration thereof, if necessary. Fresh rare earth and ruthenium precursor, Lewis base promoter and/or solvent, can be intermittently added to the recycle stream or directly to the reaction zone, if needed.

Many embodiments of the ruthenium carbonyl complex, rare-earth complex, Lewis base promoter and solvent combinations encompassed by this invention are sufficiently stable to allow repeated use of the catalyst system. This is especially noted when the promoter is an alkali metal halide, particularly and preferably an alkali metal iodide. For example, the process of this invention can be continuously operated in a pressure reactor into which is continuously fed synthesis gas. The velocity of the synthesis gas is sufficient to strip products of the reaction out of the reactor leaving behind in the reactor the catalysts complex, Lewis base and solvent combination. The products are separated from the unreacted synthesis gas and the synthesis gas is recycled to the reactor. The products, in this embodiment, are recovered free of catalysts, Lewis base and solvent. In this embodiment, the catalyst need not be removed from the reactor to a recovery zone for separating product. Thus a catalyst treatment step is avoided.

PREPARATION EXAMPLE

The following procedure was employed in all of the Examples which follow: a 150 ml capacity Autoclave Engineers stainless steel reactor equipped with a magnetically-driven stirring turbine was charged with a mixture of solvent, ruthenium, as triruthenium dodecacarbonyl, an alkali metal halide, and a rare earth complex under a nitrogen atmosphere. The reactor was sealed and then charged with carbon monoxide to a pressure of 500 psig. Heat was applied to the reactor and its contents; when the temperature of the mixture inside the reactor reached the designated reaction temperature a mixture of carbon monoxide and hydrogen was added to bring the pressure to the specified reaction pressure. Additional gas was added when the pressure inside the reactor dropped by 500 psig, so as to maintain the reaction pressure at ±500 psi of the designated pressure. The reaction temperature was generally maintained until a standard amount of gas had been consumed, usually corresponding to a total change in pressure (with additions) of 6000 psig. After the reaction period, the vessel and its contents were cooled to room temperature, the excess gas vented, and the reaction mixture was removed for analysis by gas chromatography.

Although the invention has been described in some detail, it is not intended to be limited thereby. The following examples illustrate somewhat preferred embodiments of the invention and are not limitative of scope.

EXAMPLE 1

In order to demonstrate the activity of a catalyst system of the invention as compared to a system having only a ruthenium catalyst, tests were carried out in accordance with the procedure of Preparation Example 1. The test runs were conducted under the following reaction conditions:

| Ingredients | Amounts |
| --- | --- |
| triruthenium dodecacarbonyl (Ru) | 6 mmol[a] |
| cerium acetylacetonate (Ce) | 6 mmol |
| tri n-propylphosphine oxide solvent | 75 ml |
| Iodine (I$_2$) | 4 mmol |

[a]Ru atom basis

| Reaction Parameters | |
| --- | --- |
| Pressure | 12,500 psia |
| H$_2$/CO ratio | 1 |
| Temperature | 230° C. |

In run 1 only ruthenium catalyst was employed, while in run 2 a co-catalyst system of the invention was employed. In the following table, the identity of the products formed during the test runs and the rates of product formation in moles per liter per hour is provided:

TABLE 1

| | | Mhr$^{-1}$ | | |
| | | Rates (Hr$^{-1}$) | | |
| Run | Catalyst | OHCH$_2$CH$_2$OH | Methanol | Ethanol |
| --- | --- | --- | --- | --- |
| 1 | (Ru) | — | 1.35 | 2.81 |
| 2 | (Ru) + (Ce) | 0.16 | 4.76 | 1.27 |

The test results show the enhancement in total moles of product formed when employing the process of the invention.

EXAMPLE 2

In order to further demonstrate the unexpected enhancement in product yield engendered by adding a rare-earth catalyst of the invention to the catalyst system as set forth in U.S. Pat. No. 4,434,247, a series of six (6) test runs were conducted in accordance with the procedure of Preparation Example I. The results are reported in Table 2.

In Table 2, run 3 is a comparative example showing the activity of a ruthenium catalyst in the absence of a rare-earth co-catalyst of the invention.

Run 4 illustrates that added KCl has little effect on catalyst activity or selectivity of a ruthenium-iodide catalyst.

For the following runs set forth, readily available lanthanide trichloride compounds were employed as co-catalysts. It has been found that such trichloride salt compounds can lower the activity of ruthenium-iodide systems by possible generation of strong acids, such as HCl, as shown in Run 5. To nullify that problem, a base, as K$_2$CO$_3$ is added. Any HCl produced would be converted to KCl. As noted in Run 4, KCl has little or no detrimental effect on the process. Runs 6 and 7 illustrate that when sufficient K$_2$CO$_3$ is added to neutralize all HCl theoretically produced from the CeCl$_3$, best results are obtained. At the K$_2$CO$_3$/MCl$_3$ ratio of 1.5- the theoretical ratio assuming complete reduction or alcoholysis of the lanthanide chloride- best reaction rates were attained.

In Run 8 the process was conducted without any ruthenium catalyst and no alcohol products were recovered. The reaction conditions for runs 3–8 were as follows:

| Ingredients | Amounts |
| --- | --- |
| triruthenium dodecalcarbonyl (Ru) | 6 mmols[a] |
| sodium iodide | 18 mmols |
| N—methylpyrrolidone | 75 ml |

[a]Ru atom basis

| Reaction Parameters | |
| --- | --- |
| Pressure | 12,500 psia |
| Temperature | 230° C. |
| Ratio $H_2/CO$ | 1 |

The results of runs 3–8 is set forth in Table 2 as follows:

TABLE 2

| Run | Co-Catalyst | Amount (mmol) | Additive | Amount (mmol) | E.G.[1] | Rates Mhr$^{-1}$ MeOH[2] | EtOH[3] |
| --- | --- | --- | --- | --- | --- | --- | --- |
| 3 | None | — | — | — | 0.77 | 5.37 | 0.28 |
| 4 | " | — | KCl | (9) | 0.51 | 5.26 | — |
| 5 | CeCl$_3$ | (3) | — | — | — | 0.36 | 0.12 |
| 6 | CeCl$_3$ | (3) | K$_2$CO$_3$ | (3) | 0.18 | 7.10 | 0.55 |
| 7 | CeCl$_3$ | (3) | K$_2$CO$_3$ | (4.5) | 0.28 | 11.52 | — |
| 8 | CeCl$_3$ (no Ru) | (6) | K$_2$CO$_3$ | (9) | — | — | — |

[1]EG is ethylene glycol
[2]MeOH is methanol
[3]EtOH is ethanol

EXAMPLE 3

In order to demonstrate the effects of the various rare-earth trichloride co-catalysts on the process of the invention a series of runs was conducted and the results reported in accordance with the procedure of Example 2. Unless otherwise indicated in Table 3 reporting the test results, the ratio of K$_2$CO$_3$ to MCl$_3$, (where M=rare earth element) was 1.5. In run 9 only the ruthenium catalyst is employed.

TABLE 3

| Run | MCl$_3$ | Amount | EG | MeOH | EtOH |
| --- | --- | --- | --- | --- | --- |
| 9 | — | — | .77 | 5.37 | .28 |
| 10 | Y | 3 | .21 | 6.77 | .32 |
| 11 | Y | 6 | .28 | 6.48 | — |
| 12 | La | 3 | .36 | 10.77 | — |
| 13[a] | La | 3 | — | 10.50 | .67 |
| 14 | La | 6 | .24 | 15.23 | 1.43 |
| 15[a] | La | 6 | — | 9.52 | .89 |
| 16 | Ce | 3 | .28 | 11.52 | — |
| 17 | Ce | 6 | — | 7.69 | .98 |
| 18 | Ce | 6 | .13 | 8.57 | 1.41 |
| 19 | Ce | 12 | — | 3.90 | .16 |
| 20[b] | Pr | 3 | .71 | 5.71 | .67 |
| 21[b] | Pr | 6 | .61 | 6.90 | .93 |
| 22 | Sm | 3 | .27 | 8.34 | .62 |
| 23 | Eu | 3 | .38 | 3.46 | .24 |
| 24 | Eu | 6 | .13 | 2.27 | .39 |
| 25 | Gd | 3 | .13 | 3.78 | .13 |
| 26 | Gd | 6 | .29 | 7.54 | — |
| 27 | Tb | 3 | .10 | 5.05 | — |
| 28 | Tb | 6 | .15 | 3.51 | .17 |
| 29 | Dy | 3 | .08 | 2.54 | .13 |
| 30 | Dy | 6 | .08 | 3.05 | .11 |
| 31 | Ho | 3 | .11 | 2.78 | — |
| 32 | Ho | 6 | .21 | 2.86 | .16 |
| 33 | Er | 3 | .21 | 7.37 | .51 |
| 34 | Er | 6 | .18 | 6.30 | .51 |
| 35 | Tm | 3 | .10 | 8.38 | .11 |
| 36 | Yb | 3 | .22 | 10.77 | 1.53 |
| 37 | Yb | 6 | .29 | 18.79 | 1.77 |
| 38 | Lu | 3 | .16 | 9.95 | 1.09 |
| 39 | Lu | 3 | — | 11.19 | .65 |
| 40 | Lu | 6 | .08 | 8.30 | 1.13 |
| 41 | Hf | 3 | .39 | 7.78 | — |
| 42 | Hf | 6 | — | 1.89 | .65 |

[a]K$_2$CO$_3$/MCl$_3$ = 1.
[b]1 mmol Rh also present.

The results demonstrate that the addition of rare-earth co-catalyst decreased the ethylene glycol production in all runs and in most cases increased both the rate of methanol production and the total activity of the catalyst system. Acitivity is seen to be highest at the begining and end of the lanthanide series.

Although results for Eu, Gd, Tb, Dy and Ho co-catalyts are less satisfactory than for the others tested, it is believed that further refinements in selection of process parameters and ingredients would improve substantially the activity of the system.

EXAMPLE IV

In order to illustrate the flexibility of the inventive process relative to production of ethanol, a series of test runs were conducted according to Example 1. The results are reported in Table 4 as follows:

TABLE 4

| Run | Additive | (mmol) | Additive | (mmol) | I$_2$ (mmol) | Rates, Mh$^{-1}$ EG | MeOH | EtOH |
| --- | --- | --- | --- | --- | --- | --- | --- | --- |
| 13 | — | | — | | 4 | — | 1.35 | 2.81 |
| 14 | LaCl$_3$ | (3) | K$_2$CO$_3$ | (4.5) | 4 | .25 | 4.03 | 2.39 |
| 15 | LaCl$_3$ | (6) | K$_2$CO$_3$ | (9) | 4 | .32 | 5.02 | 1.63 |
| 16 | LaCl$_3$ | (3) | K$_2$CO$_3$ | (4.5) | 6 | .31 | 3.22 | 5.60 |
| 17 | La$_2$O$_3$ | (3) | K$_2$CO$_3$ | (4.5) | 8 | 08 | 1.98 | 2.63 |
| 18 | LaCl$_3$ | (1.5) | — | | 4 | .41 | 2.70 | 3.73 |
| 19 | Yb$_2$O$_3$ | (1.5) | — | | 4 | .30 | 1.93 | 4.15 |

The results demonstrate that by use of the instant rare-earth co-catalyst and by controlling the acidity of the system through addition of iodine and a suitable solvent, good selectivity to ethanol is obtained.

The invention is not to be limited except as set forth in the following claims:

What is claimed is:

1. Process for preparing low molecular weight alcohols by reacting hydrogen and carbon monoxide in the presence of a homogeneous catalyst system comprising a ruthenium carbonyl complex and a rare-earth-containing complex selected from the group of compounds consisting of La, Ce, Yb and Lu solubilized in a solvent capable of maintaining said catalyst system in a homogeneous liquid phase.

2. The process of claim 1 wherein the reaction is carried out at a reaction temperature between about 100° C. to 400° C. and a reaction pressure between about 500 psia and 15,000 psia.

3. The process of claim 1 wherein the reaction temperature is between about 150° C. and 350° C.

4. The process of claim 1 wherein the reaction pressure is between about 1,000 psia and 12,500 psia.

5. The process of claim 1 wherein a Lewis base promoter of the reaction is employed.

6. The process of claim 5 wherein the Lewis base promoter is an alkali metal halide.

7. The process of claim 6 wherein the alkali metal halide is an alkali metal iodide.

8. The process of claim 7 wherein the alkali metal iodide is sodium iodide.

9. The process of claim 5 wherein the Lewis base promoter is iodide ion as obtained in-situ by addition of iodine.

10. The process of claim 1 wherein the solvent N-methylpyrrolidone.

11. The process of claim 1 wherein the solvent is tri-n-propylphosphine oxide.

12. The process of claim 1 wherein the rare-earth containing complex is a rare-earth halide.

13. The process of claim 12 wherein a base is additionally employed in the catalyst system.

14. The process of claim 13 wherein the base is potassium carbonate.

15. The process of claim 1 wherein the ruthenium carbonyl complex is triruthenium dodecacarbonyl.

16. The process of claim 1 wherein the rare-earth containing complex is a rare-earth trichloride salt.

17. The process of claim 16 wherein the rare-earth trichloride is lanthanum trichloride.

18. The process of claim 16 wherein the rare-earth trichloride is cerium trichloride.

19. The process of claim 16 wherein the rare-earth trichloride is ytterbium trichloride.

20. The process of claim 16 wherein the rare-earth trichloride is lutetium trichloride.

21. The process of claim 1 wherein the rare-earth containing complex is cerium acetylacetonate.

22. The process of claim 1 wherein the rare-earth containing complex is $La_2O_3$.

23. The process of claim 1 wherein the rare-earth containing complex $Yb_2O_3$.

24. The process of claim 1 wherein the low molecular weight alcohols include methanol and ethanol.

25. The process of claim 1 wherein the ruthenium complex catalyst is present in amounts between about $10^{-6}$ to 30 weight percent, based on the total weight of the catalyst system.

26. The process of claim 1 wherein the ruthenium complex catalyst is present in amounts between about $10^{-3}$ to 10 weight percent based on the total weight of the catalyst system.

27. The process of claim 1 wherein the rare-earth containing complex is present in a weight ratio to the ruthenium complex catalyst of from 0.01:1 to 100:1.

28. The process of claim 27 wherein the weight ratio is 0.1:1 to 10:1.

29. The process of claim 1 wherein the molar ratio of hydrogen to carbon monoxide is between about 1:40 to 40:1.

30. The process of claim 1 wherein the molar ratio of hydrogen to carbon monoxide is between about 10:1 to 1:10.

* * * * *